(12) United States Patent
Reinhold

(10) Patent No.: US 6,709,596 B1
(45) Date of Patent: Mar. 23, 2004

(54) DEVICE, METHOD AND SYSTEM FOR REVERSIBLY TRAPPING AND ISOLATING CARBOHYDRATES

(75) Inventor: Vernon N. Reinhold, Lee, NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 10/114,693

(22) Filed: Apr. 4, 2002

(51) Int. Cl.[7] .............................................. B01D 15/08
(52) U.S. Cl. ....................... 210/635; 210/638; 210/656; 210/198.2; 210/502.1; 536/127
(58) Field of Search ................................ 210/635, 656, 210/198.2, 502.1, 638; 436/161; 536/124, 127

(56) References Cited

U.S. PATENT DOCUMENTS

| | | | | |
|---|---|---|---|---|
| 5,075,078 A | * | 12/1991 | Osikowicz et al. | ........... 422/56 |
| 5,096,594 A | * | 3/1992 | Rabinowitz | ................. 210/656 |
| 5,308,460 A | * | 5/1994 | Mazid et al. | ................. 435/14 |
| 5,472,582 A | * | 12/1995 | Jackson | ....................... 204/459 |
| 6,260,715 B1 | * | 7/2001 | Simard et al. | ............... 210/490 |
| 6,294,667 B1 | * | 9/2001 | Jackson et al. | ............. 536/127 |

\* cited by examiner

*Primary Examiner*—Ernest G. Therkorn
(74) *Attorney, Agent, or Firm*—Devine, Millimet & Brandi, PA; Paul Remus; Kristin Kohler

(57) ABSTRACT

Disclosed herein is a reversible carbohydrate (glycan) trap, methods and system for preparing the trap and use of the trap in preparing and trapping glycans for the study of carbohydrate structure. The device and methods assist in the structural characterization of glycans. The method traps and purifies carbohydrate structures at improved sensitivities, thereby enhancing the accuracy of a tissue or cell's complete carbohydrate composition, the glycome, (vis-à-vis proteome). Most basically, the trap device covalently binds activated glycosyl residues on a polymer specifically prepared to contain aldehydic functional groups. The trap material is formed from a carbohydrate polymer, preferably dextran, which is oxidized with periodate to introduce aldehydic groups. The oxidized dextran polymer is packable into separation colulmns or micro-tips for use as the glycan trap. Glycans treated with hydrazine, to form glycosyl hydrazyls, may then be added to the oxidized carbohydrate polymer, (ODP), trap wherein they are covalently bound to the aldehyde groups of the trap. To release the bound glycosyl hydrazyls, anhydrous hydmzine may be added at approximately room temperatures, thereby releasing the glycans as glycosylhydrazyls which may then be studied further.

14 Claims, 9 Drawing Sheets

Schiff Base Formation with Benzaldehyde

Glycosylhydrazyl (Glc-Hz) Preparation

Schiff Base Formation with Benzaldehyde

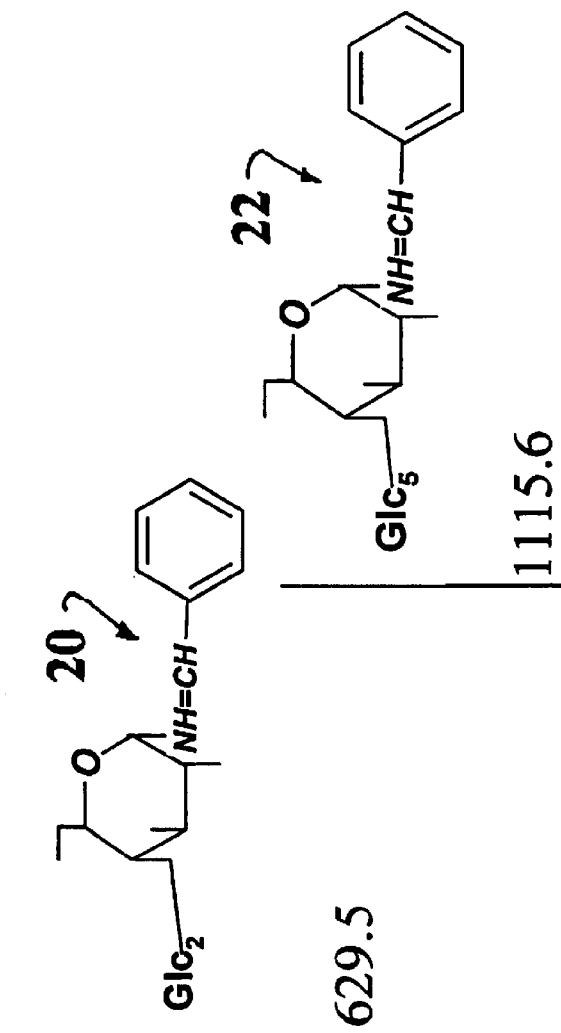
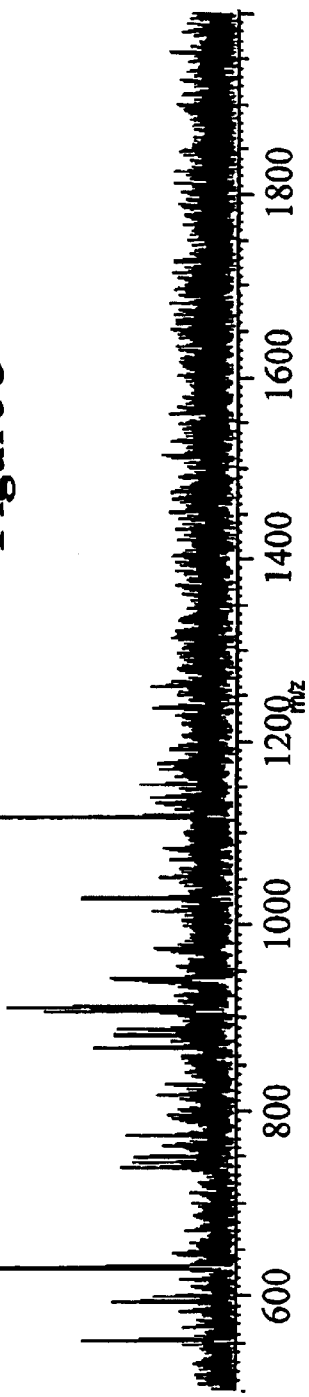
Figure 3

DEVICE, METHOD AND SYSTEM FOR REVERSIBLY TRAPPING AND ISOLATING CARBOHYDRATES

GOVERNMENT SPONSORSHIP

This Invention is funded in part by National Institutes of General Medical Sciences; GM54045.

COPYRIGHT

A portion of the disclosure of this patent document contains material which is subject to copyright protection. The copyright owner has no objection to the facsimile reproduction by anyone of the patent document or the patent disclosure as it appears in the United States Patent and Trademark Office patent file or records, but otherwise reserves all copyright rights whatsoever.

FIELD OF THE INVENTION

The function of a gene is manifested through its primary products, proteins. A measure of all proteins within a given cell or tissue has been defined as its proteome. As the structural details of biological activity are further investigated, numerous secondary gene products, (post-translational processes), are also being found as entities providing function. Foremost of these is glycosylation, a process that greatly extends the molecular specificity of cell function while adding considerable analytical difficulty for its structural characterization. This invention is a device, (hereafter called the GlycoTrap), that assists in the structural characterization of these products. More particularly, the invention relates to a method for trapping, and purifying carbohydrate structures at improved sensitivities, thereby providing a strategy for the determination of a tissue or cell's complete carbohydrate composition, the glycome, (vis-à-vis proteome). In a most basic embodiment, the GlycoTrap covalently binds activated glycosyl residues on a polymer specifically prepared to contain aldehydic functional groups.

BACKGROUND OF THE INVENTION

Genes impart function through surrogate structures. Understanding the products of gene expression and their interrelationships will provide the answers to normal and untoward cellular function and open the door to strategies that will address improvements in human health and disease.

Thus, with completion of the human genome, research is now focusing on the next level of biological function, the proteins. But, many proteins are post-translationally modified by glycosylation, and in numerous cases, these glycosylated entities are specifically responsible for function. Moreover, recent estmates indicate that more than half of all human proteins are glycosylated, and this strongly suggests extensive new efforts must be devoted to the analysis of molecular glycosylation. Mutations to a gene that is involved in glycosylation affect numerous glycoproteins and as a consequence of such mutation a multiplicity of phenotypes arise. This is exactly the case in carbohydrate deficient glycosylation (CDG) where patients suffer multiple maladies as a consequence of a single gene mutation. In contrast, a protein mutation influences only that specific protein developing a single phenotype. Therefore, the study of molecular glycosylation is integral to the study of proteins and their structures and functions.

While it is relatively easy to isolate and structurally characterize linear biopolymers, e.g., DNA, RNA, proteins, the techniques to analyze the variably linked and multiply branched carbohydrate structures remain in their infancy. When these residues are conjugated to other natural polymers structures, (lipids, proteins), the carbohydrate moieties are referred to as glycans. In glycoproteins, the glycans are attached either through hydroxy amino acids, (serine or threonine), or amide linked (asparagines), to produce O- and N-linked structures, respectively. Adding greater analytical challenge is the fact that glycans frequently exhibit heterogeneity (glycoforms) at their non-reducing terminus. Thus, a single protein gene product becomes a heterogeneous glycoprotein mixture with altered biochemical, chemical and physical properties, (pleiotrophism). Characterization of the carbohydrates on glycoproteins requires release and purification, followed by a mass spectral determination of their variable sequence, intra-residue linkage, and branching structures.

At present there are three major methods for releasing intact glycans from proteins. These include a biochemical release with endoglycosidases or a chemical release with hydrazine or strong base. The former method releases only N-linked glycans, while hydrazine treatment releases both N-, and O-linked moieties. O-linked glycans can also be specifically released with base by a classical $E_2$ elimination, (elimination second order).

Importantly, both enzymatic and chemical procedures are quantitative, and all released structures expose an identical hemiacetal, reducing terminus that provides a single chemical approach for covalent capture. Such covalent capture includes all glycoforms irrespective of variant non-reducing termini. Lectins are naturally occurring protein receptors, (natural traps), for carbohydrate structures with binding specificity for non-reducing epitopes within glycan structures. Unfortunately, with their exacting specificity, any single lectin would be ineffective in capturing all glycoforms existing on glycoproteins. Columns with combinations of lectins have been proposed, but such strategies have obvious constraints and presuppose one knows the sample structure before analysis. Furthermore, lectins are relatively difficult to isolate, and expensive to at purchase.

Robotic high throughput techniques to characterize proteins utilize 2D gels to separate the total proteome. This important chromatographic separation provides discrete spots for proteins, but the resulting "spots" greatly spread due to the glycan heterogeneity of glycoproteins and this results in diminished sensitivity when using 2D gels on glycoproteins. Moreover, since additional analytical steps are required to fully sequence the glycan, larger amounts of material are required vis-à-vis proteins. Equally as important to specific trapping of glycans is facile and quantitative release for subsequent structural characterization. Thus, there is great need to develop sample handling and trapping strategies to facilitate the study of a cell's glycome at the sensitivities extant for the proteome.

SUMMARY OF THE INVENTION

The invention is a device, method and system for trapping and releasing trace amounts of carbohydrate material for structural analysis. The strategy couples sample activation with hydrazine, followed by attachment of activated sample to an aldehydic polymer. The general approach is comparable to 2D gel proteome analysis with interceding steps for glycome characterization. In this way robotic procedures can be used to image, cut, and excise spots to a digestion tube where protein reduction, alkylation and proteolysis is carried out. The glycopeptides in such tubes are treated with hydrazine to release all glycan residues and the mixture is dried. The mixture of peptides and glycopeptides is taken up in acetonitrile/water and passed through a coupled GlycoTrap and, if desired for proteome analysis, C-18 micro-tip column. Glycans are trapped in the first column and the peptides are passed on to the second C-18 column and trapped. All extraneous debris transits through both columns. The coupled columns are separable and the respective glycans and peptide components are then separately released for further chemistry and mass spectral analysis.

Glycans are again released from the trap by hydrazinolysis, thereby forming hydrazyl compounds. This can be accomplished with hydrazine at approximately room temperatures. While the chemistry of the invention alone is relatively simple, the invention provides a desired, but previously unavailable, inexpensive, easy-to-prepare device and method for capturing and releasing glycans. The device and procedures effectively isolate trace amounts of sample devoid of extraneous background that currently diminishes detecting sensitivity.

Thus, one aspect of the invention is to provide a method and device for separating and isolating glycans and other carbohydrate moieties for structural analysis.

Another aspect of the invention is to provide a method and device for reversibly trapping and releasing carbohydrate material for analysis.

A further aspect of the invention is to provide a relatively quick and inepensive method and device for isolating glycans and other carbohydrate moieties for analysis.

Yet another aspect of the invention is to provide a method and device for facile and quantitative isolation of glycans and other carbohydrate moieties, which can be coupled with a device for trapping and isolating protein and peptide materials.

A still further aspect of the invention is to provide a method for use with small sample amounts such as those present in a 2D gel spot Another aspect of the invention is to provide a method and device that can be used with a mixture of carbohydrate and protein material, and which effectively separates the two for separate analysis.

A still further aspect of the invention is to provide a method and device for separating and isolating glycans and other carbohydrate moieties that can be used with currently available robotic laboratory equipment.

These and further aspects of the invention will become apparent to one of ordinary skill in the art upon study of the accompanying description and figures.

BRIEF DESCRIPTION OF THE DRAWINGS

FIG. 3. Mass spectral analysis of Shiff base products when benzaldehyde is reacted with a trisaccharide and a hexasaccharide.

DETAILED DESCRIPTION OF THE INVENTION

Figure 1:
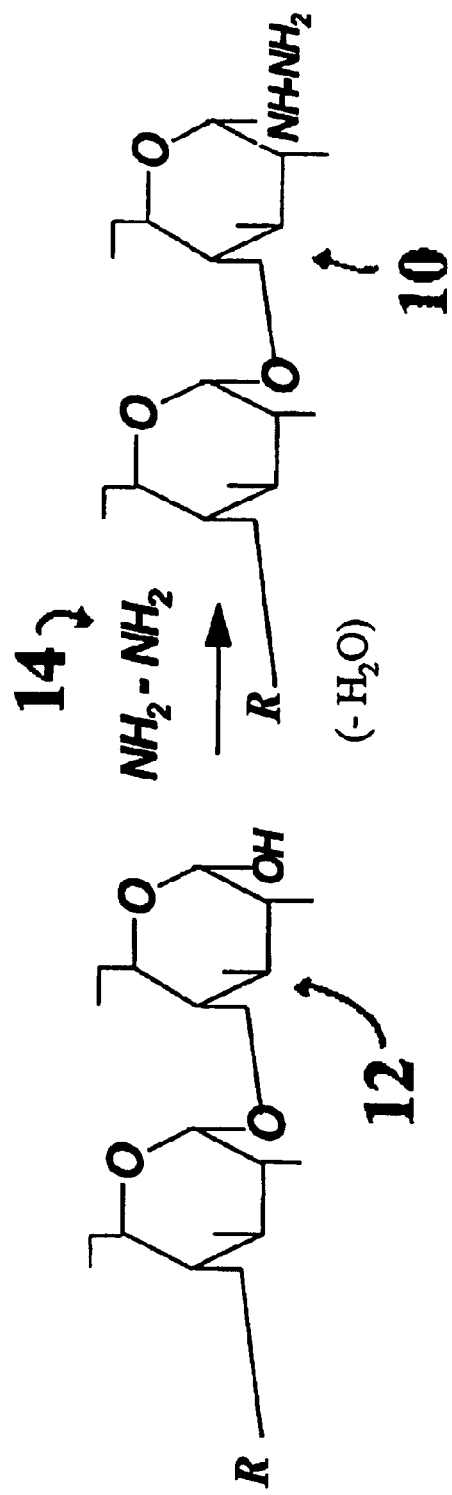
FIG. 1. A schematic chemical illustration of the procedure used to form hydrazyls.

Referring now to the figures, in which like reference numerals refer to like element throughout, a basic embodiment of the invention is a device, method and system for trapping and releasing trace amounts of carbohydrate material for structural analysis. The device is referred to generally as the "GlycoTrap". The strategy couples free reducing-end carbohydrate samples activated with hydrazine, and attached to an aldehydic polymer. The general approach is compatible to 2D gel protein analysis with interceding steps for carbohydrate characterization. In this way robotic procedures can be used to image, cut, and excise spots from a gel to a digestion tube where protein reduction, alkylation and proteolysis is carried out. The glycopeptides in such tubes are treated with hydrazine to release all glycan moieties and the mixture is dried. This step is shown schematically in FIG. 1. The mixture of aminoacids and glycans is taken up in acetonitrile/water and passed through the GlycoTrap which contains oxidized carbohydrate polymer OCP. The oxidized carbohydrate polymer in this particular example is an oxidized dextran polymer ODP, coupled with a C-18 micro-tip column. A dextran polymer is the preferred, but non-limiting, polymer shown in the examples, and is a carbohyrate polymer isolated from seaweed. However, other carbohydrate polymers, such as starches can also be used to make a trap of the present invention, thus although a dextran polymer is shown in the examples, the trap of the present invention is not to use of a dextan polymer. Glycans or other carbohydrate materials are trapped in the first (OCP) column and the amino acids are passed on to the second C-18 colon. All extraneous debris transits through both columns. The coupled columns are then separated and the respective glycans and/or other carbohydrate materials, and amino acids are separately released for further chemistry and mass spectral analysis.

Figure 9:
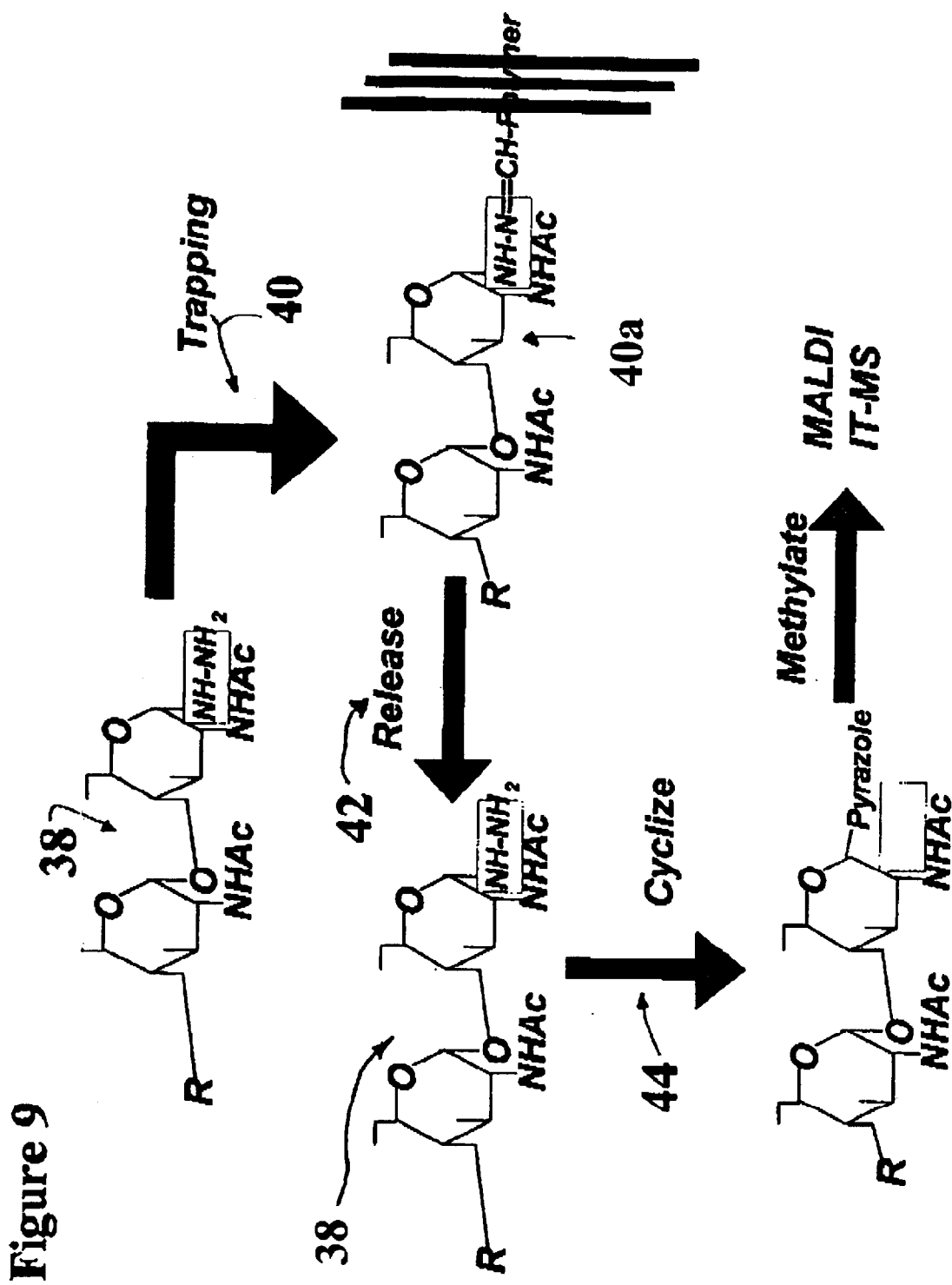
FIG. 9. Schematic illustration of the method and system of the invention

Condensed glycans, and/or other carbohydrate materials, are released from the GlycoTrap by hydrazinolysis, thereby forming glycosyl hydrazyl compounds (Gz). This is accomplished with hydrazine at approximately room temperatures of about 20–25 degrees C. A schematic illustration of an embodiment of the whole system and method of the invention is shown in FIG. 9.

Figure 5:
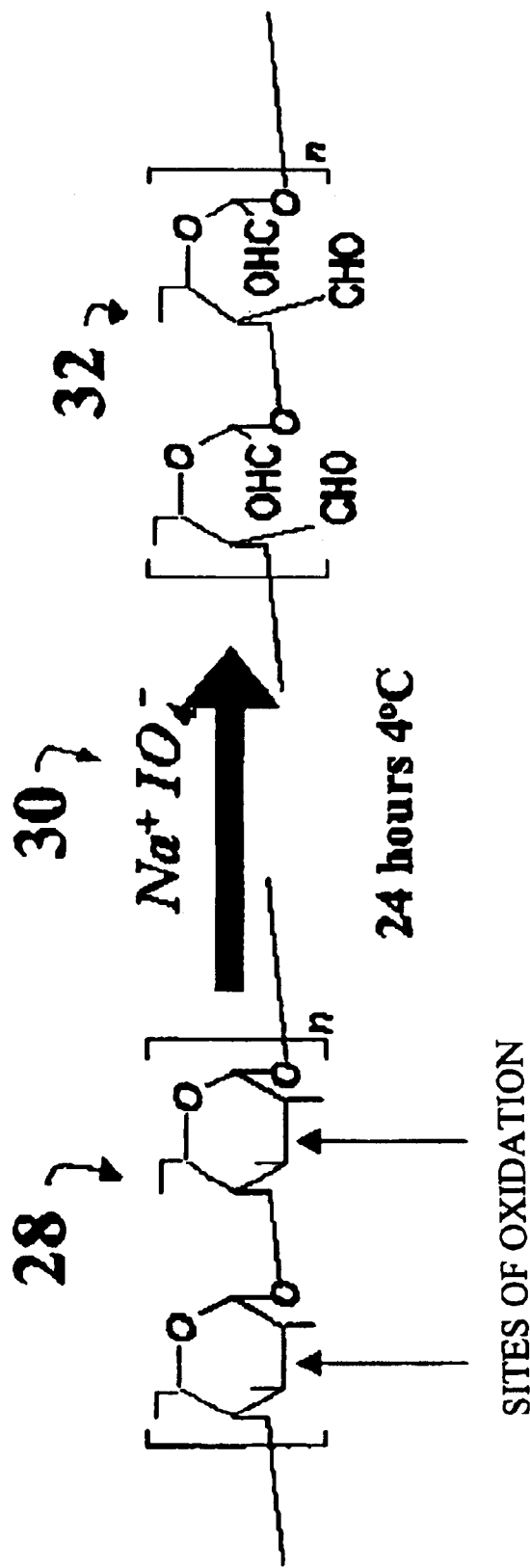
FIG. 5. Schematic illustration showing dextran polymer preparation with sodium periodate to generate multiple aldehydic groups. This oxidized dextran polymer (ODP) is subsequently used to trap the hydrazyls as described in FIGS. 1 and 2.

The invention takes advantage of the single chemical feature common to all free and released oligosaccharides, their reducing hemiacetal terminus. From here on, the term "glycans" will generally be used, however, any and all carbohydrate materials that have a reducing terminus are trappable using the present invention. Activation of this terminus with hydrazine and coupling to the OCP covalently captures all glycans as Shiff bases. Although other carbohydrate polymers may be used, all examples from here on, will generally be described using a dextran polymer. The coupling is initiated through a hydrazyl interlinking residue first attached to the glycan to provide an activated moiety, (FIG. 1, 10), that rapidly couples to the carbonyl groups introduced on the dextran polymer by periodate oxidation, (FIG. 5). The polymer was prepared by periodate oxidation of a dextran polymer to yield an aldehydic polymer and was then packed in a micro-tip or other capilary-size column. The reaction product of glycosyl hydrazyls is a Shiff base linked to the ODP substrate. Release from the ODP is accomplished by hydrazinolysis at approximately room temperature. Amino acids are not trapped on the ODP, thus providing a method and device for selective isolation of carbohydrates.

In the experiments shown below, the glucose oligosaccharides, (trisaccharide, hexasaccharide), were used as representative structures to evaluate the chemistry at the reducing terminus, a functional group that is common to all carbohydrate structures.

FIG. 1, preparation of glycosyl hydrazyls 10. The formation of such hydrazyls can result from hydrazinolysis of glycoproteins, which cleaves the glycan moieties from glycoproteins. Formation of these hydrazyls can also be accomplished by the addition of hydrazine 14 to any carbohydrate with a reducing (hemiacetal) terminus. Such a representative carbohydrate is shown as molecule 12. The result is a hydrazyl analog 10 appropriate for aldehyde condensation. Samples prepared in this way will covalently bind in the trapping device of the invention.

One of ordinary skill in the chemical arts would know, and be able to prepare, hydrazyl derivatives of carbohydrates without undue experimentation. Exact quantities and concentrations of reagents would depend on the particular experiments being carried out, and would be optimized by the practitioner. Thus, for simplicity, only the reaction in general is illustrated.

Figure 2:
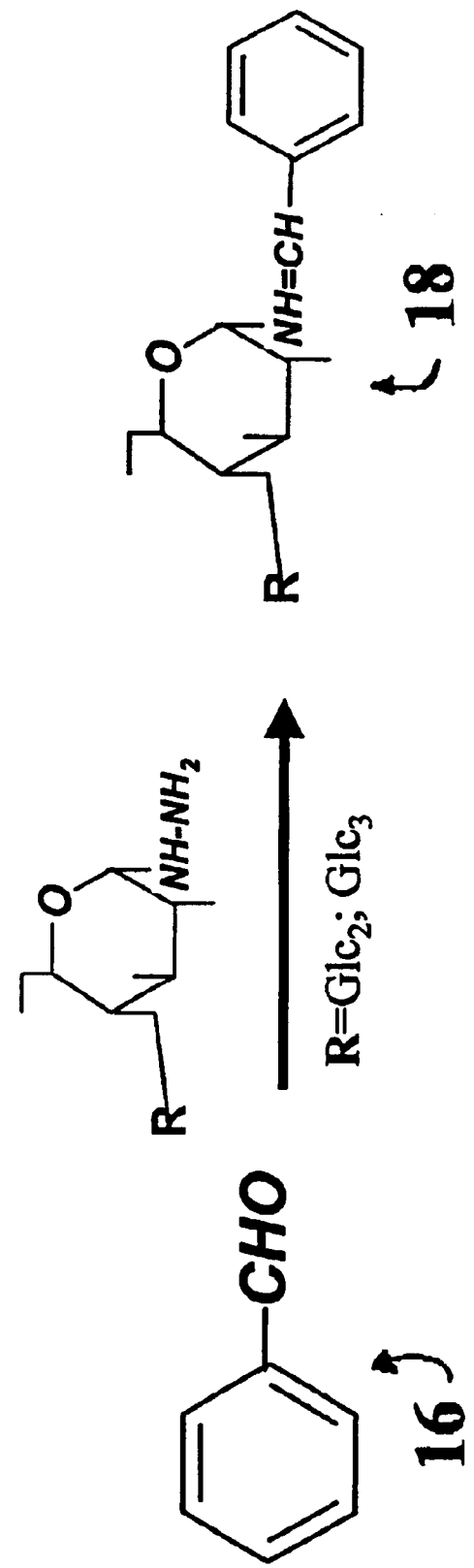
FIG. 2. A schematic chemical illustration outlining the condensation product, (Shiff base), of a hydrazyl (10) analog when reacted with an aldehyde, in this example benzaldehyde (16).

FIG. 2, Shiff base condensation products. FIG. 2 illustrates experiments performed to confirm that an aldehyde reacts with a glycosyl hydrazyl analogs. In this case benzaldehyde 16 was used as an example with glycosyl hydraryl 10 resulting in a Schiff base 18. The chemistry illustrated in FIG. 2 is the basis for glycan trapping of the present invention and illustrates the chemistry involved. Although the exact details of concentrations and quantities of reagents are not shown, again, the chemistry itself is known and one of ordinary skill in the art would be able to perform the illustrated experiments without undue effort.

FIG. 3, benzaldehyde condensation with activated hydrazyl moieties. This mass spectrum shown in FIG. 3 confirms the chemistry illustrated in FIG. 2, indicating these functional groups would be appropriate for glycan trapping when attached to a polymer. The peak at m/z 629.5 is the ion representing the Shiff base 20 formed with benzaldehyde and the hydrazyl trisaccharide. The peak at m/z 1115.6 is the ion representing the Shiff base adduct 22 with the hydrazyl hexasaccharide.

Figure 4:
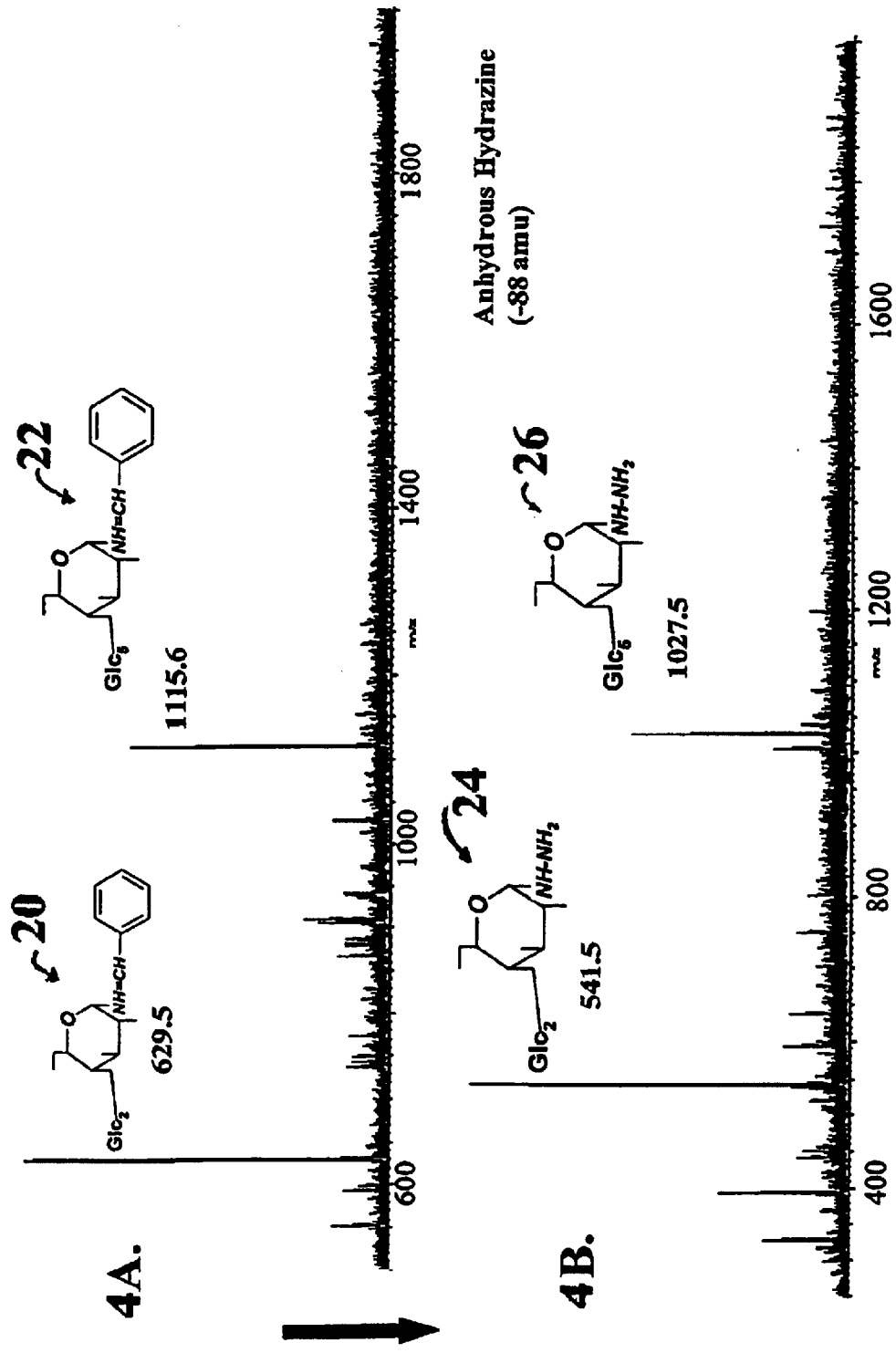
FIGS. 4A and 4B. Mass spectral analysis of Shiff base products (4A, condensation) and release (4B, hydrazinolysis).

FIGS. 4A and 4B, release of Shiff base products by hydrazinolysis. These mass spectra evaluated the ability to release Shiff base adducts by hydrazinolysis. MS of the benzaldehyde adducts 20, 22 (FIG. 4A) indicated their quantitative formation. These products were treated with anhydrous hydrazine and the products analyzed by MS, (FIG. 4B). The spectrum indicated the glycans could be effectively released as free hydrazyls. FIG. 4b illustrates and confirms the release chemistry using hydrazinolysis on the Shiff base adducts 20, 22 at approximately room temperatures of about 20–25 degrees C. The peak at m/z 541.5 is the hydrazyl trisaccharide 24, and the peak at m/z 1027.5 is the hydrazyl hexasaccharide, 26. The addition of hydrazine, at elevated temperatures, (FIG. 4B), released the glycans from the Shiff base, thus strongly suggesting comparable release of glycoproteins glycans from aldehydic polymers. Again, the m/z 541.5 peak 24 corresponds to the m/z 629.5 ion 20 of FIG. 4A, following release hydrazinolysis. Similarly the m/z 1027.5 ion 26 corresponds to the m/z 1115.6 peak 22, following release hydrazinolysis. Thus, facile condensation and release chemistry has been combined in a novel, useful, and needed way, resulting in the GlycoTrap device and method of the present invention. The temperatures of condensation and release are relatively mild (approximately room temperature) and highly amendable to robotic technology. As with the initial hydrazinolysis step, the release hydrazinolysis involves chemistry known in the art. One of ordinary skill in the art would be able to perform and optimize the release hydrazinolysis reaction without undue experimentation.

FIG. 5, preparation of an aldehydic polymer for trapping. The scheme in FIG. 5 illustrates a corner stone of the invention, formation of an oxidized carbohydrate (and in this particular example, dextran) polymer trapping material to capture glycans from complex biological matrices, a process that will lower backgrounds and allow much improved sensitivity. Periodate oxidation is used to open the C2–C3 pyran bond to form the two aldehyde groups for each glucosyl monomer. This is well known chemistry and was established over 100 years ago. However, the known procedures and chemistry as described herein transform a conventional dextran (or other carbohydrate) resin into an aldehydic polymer that can be packed into columns or micro-tips. FIG. 5 outlines the procedures to prepare the aldehyde compound used to capture glycans. In the present invention, the dextan resin 28 is oxidized with sodium periodate, step 30, at the cis-glycol positions of each monomer in the dextran polymer, resulting in oxidized dextran polymer (ODP) 32 having aldehyde functional groups which are used to covalently bind and trap glycosyl hydrazyls as Shiff bases. If oxidation of the polymer is not complete or sufficient, the periodate oxidation step may be repeated on the polymer to achieve complete oxidation. Although sodium periodate is shown as an example, the invention is not limited to use with sodium periodate. Other salts of periodates such as, but not limited to, sodium, potassium, cesium etc. may be used in the present invention. These various other periodates would be equally effective in forming the oxidized carbohydrate polymer, but there may be differences in the rates of their reactivity. Again, however, the chemistry is known and one of ordinary skill in the art would be able to prepare the ODP, or other OCP without undue experimentation, and thus, the reaction is illustrated only schematically.

Figure 6:
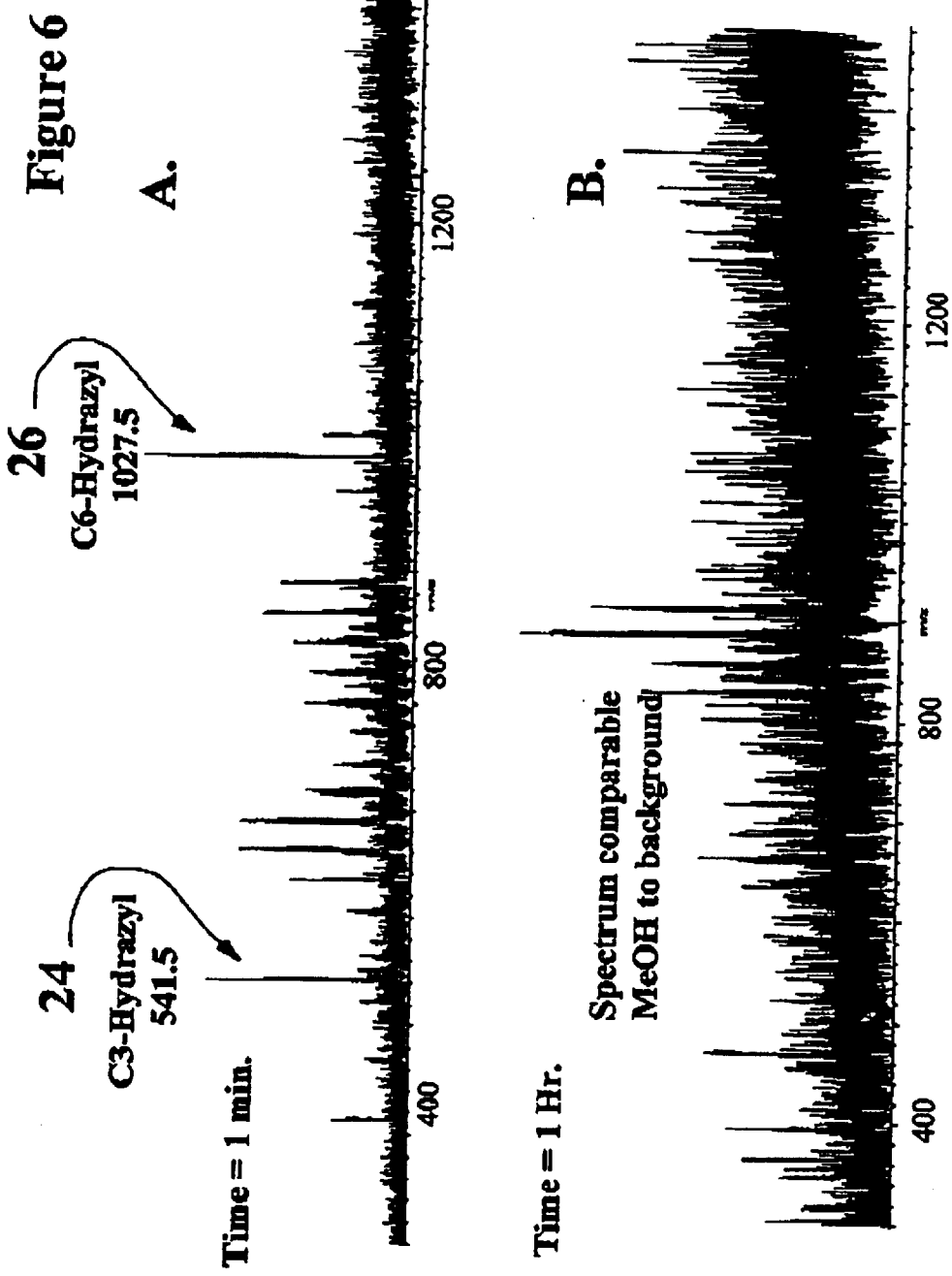
FIG. 6. Mass spectral analysis during hydrazyl reaction to the ODP resin at two time periods. Mass spectrum of supernatant at reaction time=1 min (FIG. 6A). Mass spectrum of supernatant (FIG. 6B) at time=60 min. Trapping was complete in one hour at room temperature.

FIGS. 6A and 6B, condensation of hydrazyls analogs to the ODP. Mass spectral analysis to follow Shiff base formation of tri-, and hexasaccharide hydrazyls to the ODP. Reaction supernatant removed for analysis at two time periods, 1 and 60 min, (FIGS. 6A and 6B, respectively). FIG. 6a illustrates that the glycosylhydrazyls are not completely attached to the ODP resin after 1 minute. However, FIG. 6b indicates complete attachment after 1 hour, e.g., absence of glycosylhydrazyls ions (or peaks) at m/z 541.5 (peak 24) and m/z 1027.5, (peak 26). The analysis was performed to confirm the facile conditions of glycosylhydrazyl Shiff base formation to the ODP. The MS spectrum of FIG. 6b is comparable to the spectrum obtained from an injection of methanol (MeOH) only, (background). The exact conditions and optimal time for condensation may vary somewhat with each sample but these results strongly suggest the hydrazyls attach rapidly. One of ordinary skill in the art would be able to determine the amounts to load on a column, the optimal solvent and time to leave the sample on the column etc., depending on the sample(s) being studied. The molar equivalents of reacting groups are theoretically in large excess of any analytical amount of sample added which may contribute to enhanced reactivity. With capillary-sized columns, the sample will remain on the column until positive pressure is applied to force the sample through the column, thus the sample can be left on the column long enough for all the glycans to be bound to the ODP or other OCP.

Figure 7:
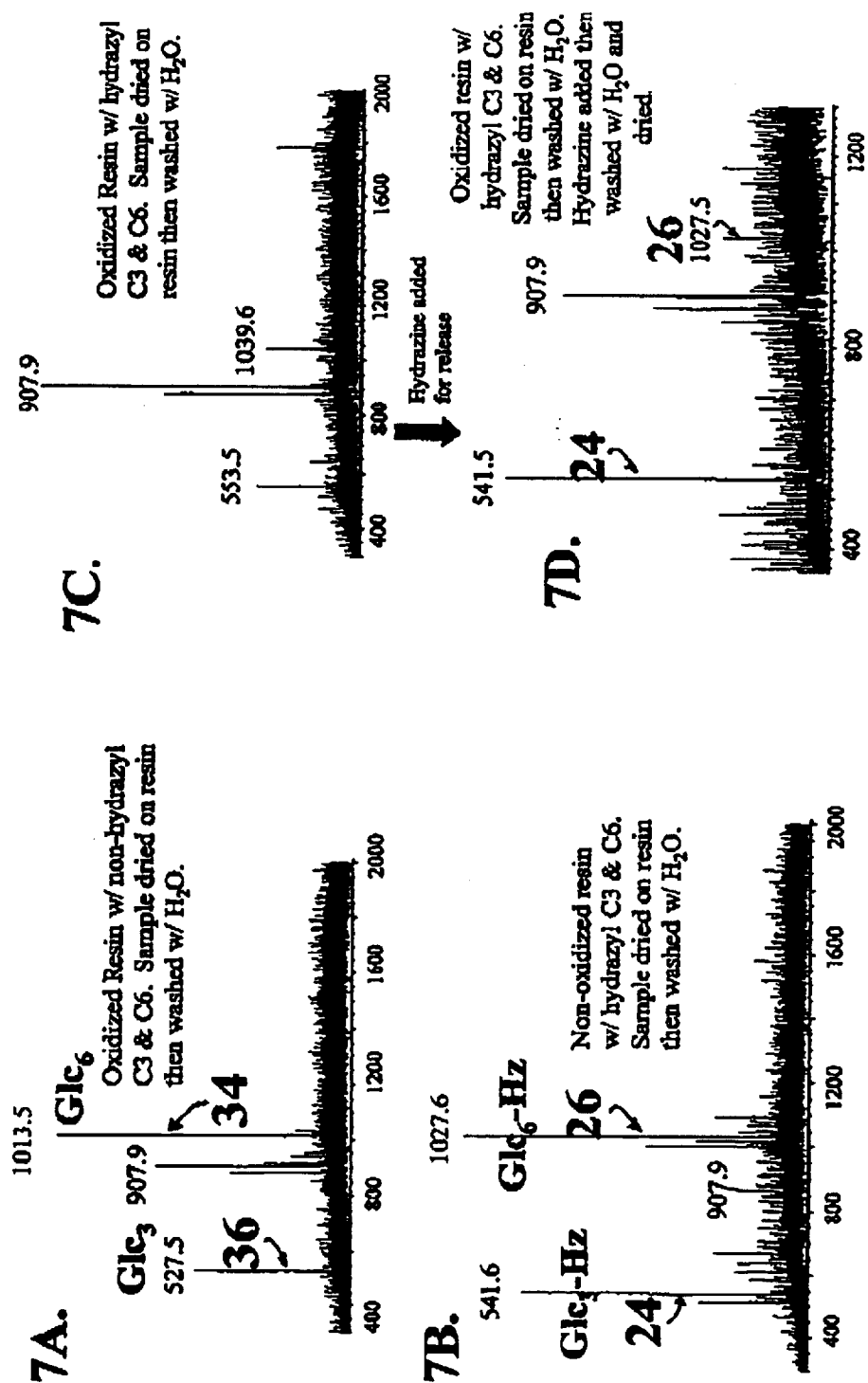
FIG. 7. Mass spectra (MS) obtained under varying normal and control conditions.
  A.) MS of extract using oligosaccharides not prepared as hydrazyls.
  B.) MS of extract using glycosyl hydrazyls and an unoxidized dextran polymer.
  C.) MS of extract using glycosyl hydrazyls with ODP; (normal method).
  D.) MS of extract following hydrazinolysis to release condensates.

FIGS. 7A–D, tests of reacting components in the ODP condensation and release. Mass spectral analyses were performed to test the specificity of functional groups, and their participation in the condensation and release sequence. The absence of a hydrazyl moiety on the glycan (FIG.7A) or the absence of aldehydic groups on the dextran polymer, (FIG. 7B), clearly shows ineffective trapping. In FIG. 7A, glycans in the absence of activation, (e.g., no hydrazyls), provide MS evidence for the tri-, and hexasaccharide ions at m/z 527.5 an m/z 1013.5, ions 34 and 36, respectively. There was no binding to the column. The experiment shown in FIG. 7B used glycosylhydrazyls in the absence of an oxidized resin (ODP), and the tri-, and hexasaccharide hydrazyls are indicated by the ions 24 and 26, respectively. Again, there was no binding to the column. In FIG. 7C, the mass spectrum showed an absence of any related products using a standard GlycoTrap with both ODP and activated glycosylhydrarls. Finally, in FIG. 7D, the mass spectrum shows the presence of the tri-, and hexasaccharide ions, (peaks 24 and 26), after a second (release) hydrazinolysis, as the expected hydrazinolysis products, indicating their release from the ODP as glycosylhydrazyls.

Background ions attributed to column bleed are apparent at m/z 907.9. Two other extraneous ions are also noted in FIG. 7C, m/z 535.6 and m/z 1039.6. These fall 14 amu lower than the expected glycosylhydrazyls and may be explained as ammonia contaminates in the hydrazine reagent. These analogs are unable to form Shiff bases with the resin. The column background problems and all chemistries described may be modified, by the practitioner, to obtain optimal conditions.

Figure 8:
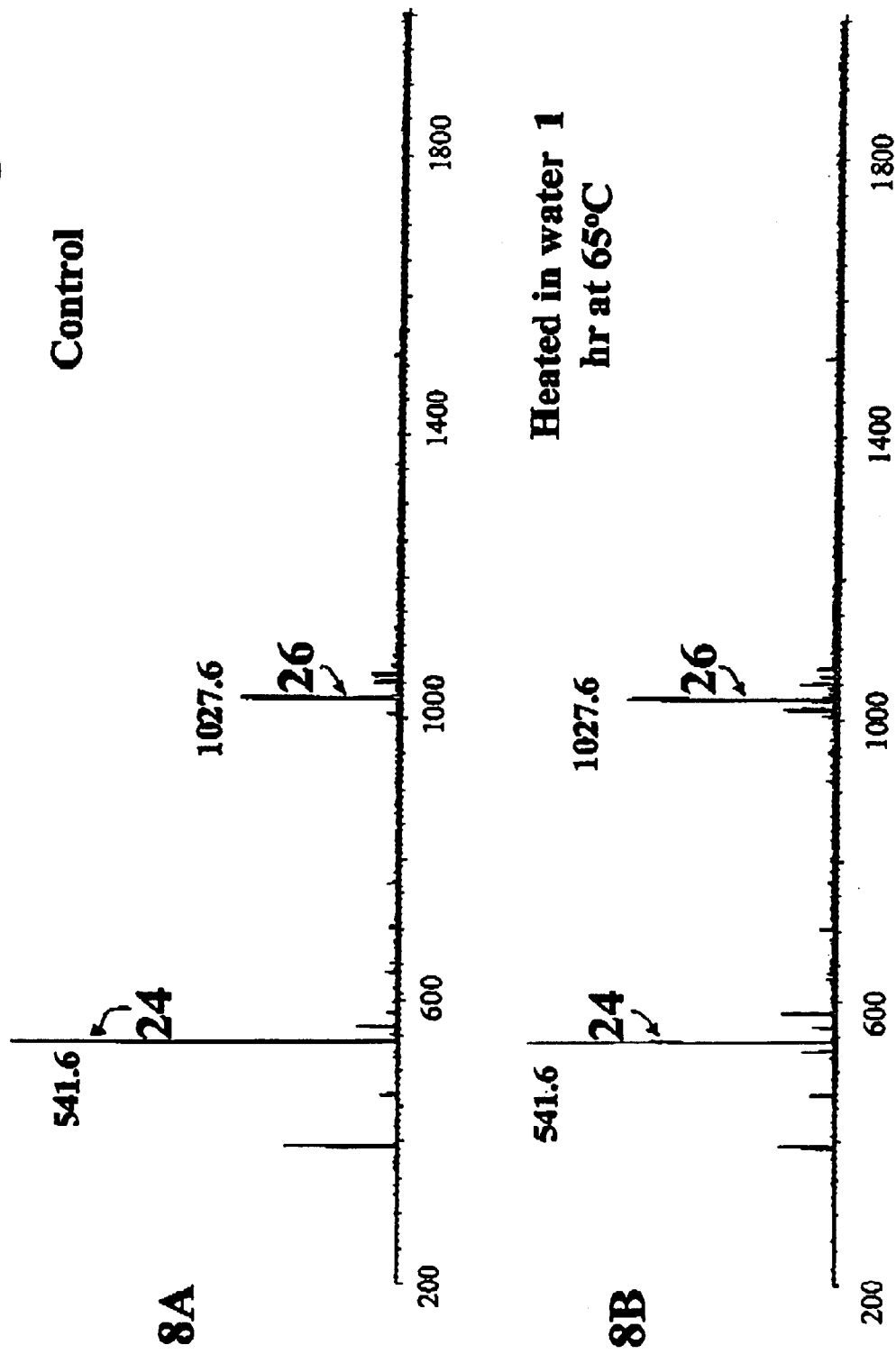
FIG. 8. MS of condensate water extracts following control (SA) and heating (8B).

FIGS. 8A and 8B, stability in aqueous solutions. These spectra of tri-, and hexasaccharide hydrazyls indicate their stability in aqueous solvents. FIG. 8A shows a control experiment with the expected ions 24 and 26, respectively. The spectrum in FIG. 8B was taken after heating the same ions 24 and 26 in water for one (1) hour at 65 degrees Centigrade. As noted by the ion peaks 24 and 26, respectively, the component hydrazyls are stable under the conditions of this experiment.

FIG. 9, in-process condensation and release cycle of the GlycoTrap. This figure shows a summary of steps used in the isolation of glycans, via the present invention, for structural characterztion. Glycans prepared as hydrazyls are captured on the GlycoTrap, which provides a specific mechanism to isolate carbohydrates from dilute and contaminated solutions, wherein the isolated carbohydrates are free of extraneous cellular debris. Release of purified products from the trap by hydrazinolysis yields a derivative that can be easily cyclyzed to a terminal pyrazole. This weakly UV absorbing product can be analyzed directly or can be subjected to methylation chemistry, a technique important to detailed characterization of age and branching analysis. The rapid formation, under mild conditions, and the stable products that result provide a device and method amenable to robotic control.

The GlycoTrap device, and method of the present invention, is highly suited to the study of glycan profiles. In methods of the present invention, activation with hydrazine is necessary for trapping. Glycosylhydrazyls are also formed during direct release of glycans, (hydrazinolysis), from glycoproteins, as well as a consequence of simple addition of hydrazine to carbohydrate samples, (FIG. 2). These derivatized moieties 38 are passed through the OCP (in this example ODP) column and covalently bind to the column as Shiff base adducts, shown at step 40, with the resulting representative Schiff base shown as 40a. Release is initiated by the addition of anhydrous hydrazine at room temperature, about 20–25 degrees C., for approximately 15 minutes, as shown at step 42, with the representative released product again being the starting activated moiety 38. Released products are ideally suited for further study by pyrazole formation, shown at 44, or by removing the hydrazine adduct from the glycan. The chemistries shown schematically in FIG. 9 would be known to one of ordinary skill in the art. Any further modification or study of the glycosylhydrazyl or glycan alone would be at the option of the practitioner. The present invention simply provides a way to trap and isolate glycans for further study.

Therefore, the oxidized carbohydrate polymer trap of the present invention, in combination with hemiacetal activation of glycans, utilizes basic chemistry in a device and method that has not been previously contemplated or attempted. The trapping device of the present invention provides sample purification and detection sensitivities previously unattainable. The exact amounts and levels of retrieved sample would be determined by the samples used and conditions of the experiments performed, and would be optimized by the practitioner. The trap of the present invention allows complete capture and recovery of very small samples, typically those obtained from 2D gels, thereby enabling glycan sequencing at the level of protein characterization. Thus, the present invention will greatly aid in the study of molecular glycosylation of proteins, and extend our understanding of gene function to greater detail.

In summary, the process and device of the invention activates glycans and covalently binds them on an oxidized carbohydrate polymer column, (OCP) of the invention. In the subsequent steps the trapped residues are released and recovered for study. The methods of the invention can include trapping in serially coupled micro-tips to separate glycans from protein residues. Following standard proteome protocols, as an example, single 2D spots of a glycoprotein, (following reduction, alkylation, and proteolysis), could be treated with hydrazine and the resulting mixture passed through the GlycoTrap to capture the glycans while allowing extraneous cellular debris, proteins, and peptides to pass through to a second C-18 trap. These coupled micro-tips (OCP and C-18) could then be separated and the components released as described above. The glycan hydrazyls can be cyclyzed, methylated and further studied to characterize sequence, linkage and branching by $MS^n$.

In a more comprehensive approach, N-linked glycan attachment sites to the proteins can be determined with endoglycosidase release in the presence of O-18 water. This strategy incorporates the O-18 label which may be detected by a peptide mass shift. The identified peptide can then be isolated and sequenced by $MS^2$. The peptides eluted from the C-18 micro-tip can be profiled by MALDI-T of mass spectrometry and identified by library searching.

An additional advantage of the glycan trap and methods of the present invention is that very small sample amounts, including very dilute samples, can be effectively recovered for analysis. To date, there is no effective method or device for separating glycans from glycoproteins and trapping the glycans for further study of only the glycans. The present invention provides such a device and method. First, all of the glycans present in the sample are released from the protein by hydrazinolysis and covalently bound in the OCP trap. The GlycoTrap thereby enhances detection by concentrating dilute samples, and lowering background (eliminating cellular debris, proteins, peptides, and amino acids). The trapped glycans are then releasable in a purified form for further study and characterization. The exact amounts and detection limits will depend on each practitioner's particular samples and experimental conditions.

While the above description and examples disclose some preferred embodiments of the invention, the invention is not limited in scope by the specific example embodiments described. The described embodiments are intended as single illustrations of individual aspects of the invention, and any and all functionally equivalent methods and components are within the scope of the invention. There may be variations and modifications of the invention, in addition to those shown and described herein, that, while not specifically described, do not depart from the spirit and scope of the invention as described above and in the appended claims, and which will become apparent to those skilled in the art from the foregoing description and the results and data shown in the accompanying drawings. All such modifications are intended to fall within the scope of the appended claims.

What is claimed is:

1. A method for reversibly trapping and isolating carbohydrate moieties comprising:

treating a carbohydrate-containing sample with hydrazine, resulting in hydrazine-activated carbohydrate-containing sample;

preparing an aldehyde-containing trapping material;

packing a trapping means with said aldehyde-containing trapping material;

passing said hydrazine-activated carbohydrate-containing sample through said trapping means packed with said aldehyde-containing trapping material, thus binding and thereby trapping all hydrazine-activated carbohydrate moieties of said hydrazine-activated carbohydrate-containing sample therein;

releasing said hydrazine-activated carbohydrate moieties from said aldehyde-containing trapping material by treating said aldehyde-containing trapping material and said hydrazine-activated carbohydrate moieties trapped therein, with additional amounts of anhydrous hydrazine; and retrieving said hydrazine-activated carbohydrate moieties from said trapping means after their release from said aldehyde-containing trapping material.

2. The method of claim 1 wherein said treating a carbohydrate-containing sample with hydrazine is performed at about room temperature.

3. The method of claim 2 wherein said room temperatures are in the range of about 20 to 25 degrees C.

4. The method of claim 1 comprising: taking up said hydrazine-activated carbohydrate-containing sample in a mixture of acetonitrile and water before passing said hydrazine-activated carbohydrate-containing sample through said trapping means packed with said aldehyde-containing trapping material.

5. The method of claim 1 wherein preparing said aldehyde-containing trapping material comprises preparing an oxidized polymer by treating a polymer with periodate at the cis-glycol positions of each monomer of said polymer to form aldehyde groups at the cis-glycol positions.

6. The method of claim 5 wherein said polymer comprises a carbohydrate polymer.

7. The method of claim 6 wherein said carbohydrate polymer is a dextran polymer.

8. The method of claim 5 wherein said periodate includes sodium periodate, potassium periodate, and cesium periodate.

9. The method of claim 1 wherein said trapping means comprises a micro-tip or other capillary-sized column.

10. The method of claim 1 wherein said releasing said hydrazine-activated carbohydrate moieties from said aldehyde-containing trapping material by treating said aldehyde-containing trapping material and said hydrazine-activated carbohydrate moieties trapped therein, with additional amounts of anhydrous hydrazine is performed at about room temperatures.

11. The method of claim 10 wherein said about room temperatures are in the range of about 20 to 25 degrees C.

12. The method of claim 1 comprising coupling a second trapping means in sequence after said trapping means; and passing all material that is not trapped and bound in said aldehyde-containing trapping material through said second trapping means.

13. The method of claim 12 wherein said second trapping means comprises a C-18 micro-tip prepared to trap protein and peptide materials for study.

14. The method of claim 1 comprising removing said hydrazine from said hydrazine-activated carbohydrate moieties after said release from said aldehyde-containing trapping material and retrieval from said trapping means.

* * * * *